United States Patent [19]

Barnish et al.

[11] 4,179,520

[45] Dec. 18, 1979

[54] L- AND DL-PHENYLGLYCINES TO TREAT A DISEASE OR CONDITION ATTRIBUTABLE TO REDUCED BLOOD FLOW

[75] Inventors: Ian T. Barnish, Ramsgate; Peter E. Cross; John C. Danilewicz, both of Canterbury; Malcolm Morville, Cliftonville, all of England

[73] Assignee: Pfizer Inc., New York, N.Y.

[21] Appl. No.: 937,940

[22] Filed: Aug. 30, 1978

Related U.S. Application Data

[62] Division of Ser. No. 834,768, Sep. 19, 1977, Pat. No. 4,148,120.

[30] Foreign Application Priority Data

Sep. 28, 1976 [GB] United Kingdom ............... 40306/76

[51] Int. Cl.² ........................................... A61K 31/24
[52] U.S. Cl. ................................................. 424/309
[58] Field of Search ......................................... 424/309

[56] References Cited

U.S. PATENT DOCUMENTS 3,976,680  2/1973  Clarke ............................ 260/471 A
4,016,205  9/1975  Kariyane ........................... 260/519

Primary Examiner—Stanley J. Friedman
Attorney, Agent, or Firm—Connolly and Hutz

[57] ABSTRACT

L- and DL-Phenylglycines of the formula

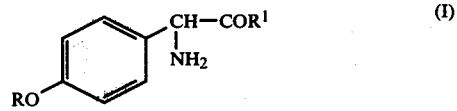

and pharmaceutically acceptable salts thereof, wherein R is hydrogen or methyl and $R^1$ is $NH_2$, OH or completes a carboxylic ester group, useful in treating certain cardiovascular diseases, diabetes and obesity.

5 Claims, No Drawings

L- AND DL-PHENYLGLYCINES TO TREAT A DISEASE OR CONDITION ATTRIBUTABLE TO REDUCED BLOOD FLOW

CROSS-REFERENCE TO RELATED APPLICATION

This application is a division of application Ser. No. 834,738 filed Sept. 19, 1977, now U.S. Pat. No. 4,148,120.

BACKGROUND OF THE INVENTION

1. Field of the Invention

The invention relates to novel use of the compounds of formula (I) in treating mammalian subjects, including humans, suffering from diseases or conditions which are characterized by reduced blood flow, oxygen availability or carbohydrate metabolism in the cardiovascular system, or other diseases involving defects in carbohydrate metabolism, particularly obesity and diabetes. The compounds of formula (I) are well known in the art and methods for optical resolution of the racemic mixtures to obtain the L-isomers have been reported in, for example, U.S. Pat. Nos. 3,976,680 and 4,016,205 and references cited therein.

2. Description of the Prior Art

As mentioned above, the compounds of formula (I) are known compounds. Methods for the preparation of racemic 2-(4-hydroxyphenyl)glycine and 2-(4-methoxyphenyl)glycine and their esters as well as the resolution of the esters into the D- and L-enantiomers are described in U.S. Pat. No. 3,976,680. The same reference provides methods for hydrolysis of the resolved esters to provide the optically active acids of formula (I).

U.S. Pat. No. 4,016,205 discloses a process for resolving D- and 1,2-(4-hydroxyphenyl)glycine and reviews the prior art chemical and enzymatic methods for the resolution of the D-isomer.

The amides of formula (I) are readily obtained, for example, from the corresponding acids via the acid chlorides by well-known methods, or from the corresponding lower alkyl esters such as the methyl ester, by treatment with ammonia as described by Neilson and Ewing, *Jour. Chem. Soc., Part C*, 393 (1966) for preparation of optically active phenylglycines.

While the DL- and D- forms of the acids of formula (I) are known in the art to be useful intermediates in the preparation of penicillins and cephalosporins, no medical or any other use has been proposed for the L-isomers of formula (I), or any medical use for the racemic forms of these compounds.

SUMMARY OF THE INVENTION

The present invention provides a novel method of treating mammalian subjects, including humans, suffering from a disease or condition attributable to reduced blood flow, oxygen availability or carbohydrate metabolism, which comprises orally or parenterally administering to said subject a blood flow, oxygen availability of carbohydrate metabolism increasing amount of the L- or DL-form of a compound of the formula

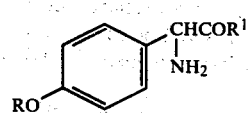

(I)

or a pharmaceutically acceptable salt thereof, wherein R is hydrogen or methyl and $R^1$ is $NH_2$, OH or completes a carboxylic ester group. When $R^1$ completes said ester group, a particularly preferred value therefore is alkoxy having from one to five carbon atoms. Especially preferred such esters of formula (I) are methyl L(+)-2-(4-hydroxyphenyl)glycinate and the corresponding isopropyl and 3-methyl butyl esters of L(+)-2-(4-hydroxyphenyl)glycine.

An especially preferred phenylglycine of formula (I) is L(+)-2-(4-hydroxyphenyl)glycine. The D-isomers of formula (I), such as D(−)-2-(4-hydroxyphenyl)glycine are substantially ineffective and the L-isomers are consequently more effective than the DL- (racemic) forms at the same dose level.

Other particularly preferred compounds are L(+)-2-(4-methoxyphenyl)glycine and L(+)-2-(4-hydroxyphenyl)glycinamide.

The invention further provides a composition of matter in unit dosage form suitable for increasing blood flow, oxygen availability or carbohydrate metabolism which comprises a pharmaceutically acceptable carrier and from about 25 to 700 mg. of the L-form of a compound of the formula (I) or a pharmaceutically acceptable salt thereof.

DETAILED DESCRIPTION OF THE INVENTION

The invention provides a novel method of treating an animal having a disease or condition attributable to reduced blood flow, oxygen availability or carbohydrate metabolism in the cardiovascular system, or other disease or condition involving a defect in carbohydrate metabolism. While certain nonmammaliam animals suffering from such diseases or conditions may benefit from treatment according to the invention, the preferred subjects are mammals, including humans. Examples of diseases or conditions attributable to reduced blood flow, oxygen availability or carbohydrate metabolism in the cardiovascular system are ischaemic heart disease, particularly angina pectoris and myocardial infarction; and cardiac failure. Regarding those diseases or conditions other than those primarily associated with the cardiovascular system and which involve a defect in the subject's carbohydrate metabolism, the compounds of formula (I) are especially effective in the treatment of diabetes and obesity.

The invention also discloses a pharmaceutical composition comprising a compound of formula (I) or a pharmaceutically acceptable salt thereof, together with a pharmaceutically acceptable diluent or carrier, said composition being in unit dosage form.

By the term "unit dosage form" as used herein is meant a physically discrete unit containing an individual quantity of the active component in association with a pharmaceutically acceptable diluent or carrier, the quantity of active component being such that at least one unit or severable fraction of a unit is required for a single therapeutical administration. In the case of severable units, such as scored tablets, at least one severable fraction such as one half or one quarter of the unit may be all that is required for a single therapeutic administration. It will be appreciated that the term "unit dosage form" does not include mere solutions except when the solutions are packaged in ingestible containers, e.g., soft capsules, or have been prepared so as to be suitable for parenteral administration, e.g., in vials of solution suitable for parenteral injection.

In said compounds of formula (I), when $R^1$ completes a carboxylic ester group, it is preferably a group of the formula —$OR^2$ wherein $R^2$ is an alkyl group having from one to five carbon atoms, a phenyl group optionally substituted by a member selected from the group consisting of alkyl having from one to four carbon atoms, alkoxy having from one to four carbon atoms, chloro, bromo and iodo; or an aryl substituted alkyl, said alkyl having from one to four carbon atoms and said aryl being a phenyl group optionally substituted by a member selected from the group consisting of alkyl having from one to four carbon atoms, alkoxy having from one to four carbon atoms, chloro, bromo and iodo. In the compounds of formula (I), when $R^1$ completes a carboxylic ester group, an especially preferred value for —$OR^2$ is alkoxy having from one to five carbon atoms. Particularly preferred such esters are methyl L(+)-2-(4-hydroxyphenyl)glycinate, isopropyl L(+)-2-(4-hydroxyphenyl)glycinate and 3-methylbutyl L(+)-2-(4-hydroxyphenyl)glycinate.

Pharmaceutically acceptable salts of compounds of the formula (I) may be addition salts with acids containing pharmaceutically acceptable anions, e.g. the hydrochloride, hydrobromide, sulphate or bisulphate, phosphate or acid phosphate, acetate, maleate, fumarate, lactate, tartrate, citrate, gluconate, succinate, p-toluenesulphonate and carbonate salts. Pharmaceutically acceptable salts of compounds of the formula (I) in which $R^1$ is OH may also be salts containing pharmaceutically acceptable cations, e.g. the sodium, potassium, calcium, magnesium and ammonium salts, and salts with amines or amino acids, e.g., the salts with arginine, N-methylglucamine, ethanolamine, choline, triethanolamine, triethylamine, piperidine, pyrrolidine or diethylaminoethylamine.

As mentioned above, the phenylglycine derivatives of formula (I) are known compounds. Methods for the preparation of the DL-compounds and their subsequent resolution into the D- and L-forms are well known (see, for example, U.S. Pat. No. 3,976,680).

The compounds of the formula (I) may be administered to patients in admixture with or dissolved in a pharmaceutically acceptable carrier selected with regard to the intended route of administration and standard pharmaceutical practice. For example, they may be administered orally in the form of tablets or capsules containing a unit dose of the compound of the formula (I) together with such excipients as corn starch, calcium carbonate, dicalcium phosphate, alginic acid, lactose, magnesium stearate, talc, or certain complex silicates. The tablets are typically prepared by granulating the ingredients together and compressing the resulting mixture to tablets of the desired size. The capsules are typically prepared by granulating the ingredients together and filling them into hard gelatin capsules of the appropriate size to contain the ingredients.

The compounds may also be administered parenterally, for example by intramuscular, intravenous or subcutaneous injection. For parenteral administration, they are best used in the form of a sterile aqueous solution which may contain other solutes, for example enough salts (e.g. sodium acetate, sodium lactate, sodium succinate or sodium chloride) or dextrose to make the solution isotonic. A pharmaceutically-acceptable organic solvent such as polyethylene glycol or ethanol may also replace part of the water. An antioxidant such as sodium metabisulphite may also be present, typically in an amount of up to 0.1% by weight. Such parenteral formulations may be prepared by conventional methods. For example, in a typical procedure involving the preparation of a succinate-containing intravenous formulation, a 0.2 molar solution of succinic acid may be mixed with a 0.2 molar solution of sodium hydroxide to give a solution of pH 5. The compound of the formula (I) is then typically dissolved in the succinate solution in an amount of 1-2% on a weight/volume basis. The resulting solution may then be sterilized, for example, by filtration through a bacteria-proof filter under aseptic conditions into sterile containers.

Alternatively, stable parenteral formulations based on isotonic saline solution may be prepared by successively dissolving an antioxidant, e.g., sodium metabisulphite, and sodium chloride in nitrogen-sparged water to give an approximately 0.1 molar sodium chloride solution, dissolving the compound of formula (I) in solution in an amount of 1-2% on a weight/volume basis and adjusting the pH to about 4 with 0.1 N hydrochloric acid. The solution is then sterilized and filled into containers as already described. Suitable containers are, for example, sterile glass vials of an appropriate size to contain the desired volume of solution, which volume will typically contain one or more unit doses of the compound of the formula (I). The compounds of the formula (I) may also be administered by the infusion of a parenteral formulation as described above into a vein.

For oral or parenteral administration to human patients, it is preferred that the dosage level of the L-form of a compound of the formula (I) will be from about 0.5 to 10 mg./kg. and especially 2 to 5 mg./kg. for a typical adult patient (50-70 kg.), said dose being administered up to 5 times a day. Thus, a typical unit dose would contain from about 25 to 700 mg. of the active compound. Tablets or capsules will preferably contain from about 25 mg. to 700 mg. of the active compound, one or more of which would be taken orally up to 5 times a day. Dosage units for parenteral administration will preferably contain from 25-700 mg. of the active compound in 5-20 ml. of solution and will thus contain from about 5 to 35 mg./ml. of the L-form of said compound of formula (I). A typical vial could thus be a 50 ml. vial containing from 5 to 35 mg. of the active compound per ml. in 30-50 ml. of solution. The expected dosage level of the DL- (racemic) form of the compounds will, of course, be higher than that of the L-form.

It should, of course, be appreciated that the physician in any event will determine the actual dosage which will be most suitable for the individual and it will vary with the age, weight and response of the patient. The above dosages are exemplary of the average host. There may, of course, be individual cases where higher or lower dosage ranges are merited.

The utility of the compounds of the formula (I) for treating disease or conditions characterized by reduced blood flow, oxygen availability or carbohydrate metabolism in the cardiovascular system, or other disease or condition involving a defect in carbohydrate metabolism, particularly diabetes and obesity, is assessed by their ability:

(1) to increase the oxidation of glucose and/or pyruvate by isolated rat muscle preparations in vitro;

(2) to increase the proportion of the active form of the enzyme pyruvate dehydrogenase (PDH) in organs of animals in vivo;

(3) to reduce oxygen demand and affect the relative utilization of carbohydrate and lipid metabolites by the electrically-paced heart of anesthetized dogs in the presence or absence of an isoprenaline stimulus; and (4) to decrease blood glucose levels in animals made diabetic by chemical lesion of the pancreas.

Activity in tests for (1) illustrates the utility of the compounds in the treatment of ischaemic heart disease, cardiac failure, maturity-onset diabetes or obesity. Activity in tests for (2) further illustrates their utility in the treatment of these diseases or conditions and, in particular, activity in an animal heart in vivo demonstrates utility in the treatment of ischaemic heart disease and cardiac failure. Activity in tests for (3) further illustrates their utility in the treatment of ischaemic heart disease and cardiac failure. Activity in tests for (4) is a further measure of their utility in the treatment of diabetes.

EXAMPLE 1

The compounds of formula (I) were tested for their ability to increase pyruvate oxidation as follows:

Diaphragm tissue is obtained from rats fed on a high fat diet similar to "Diet B" described by Zaragoza and Felber, *Horm. Metab. Res.*, 2, 323 (1970). Pyruvate oxidation by such tissue is assessed by measurement of the rate of incorporation of carbon-14 from carbon-14-labelled pyruvate into carbon dioxide in vitro, as described by Bringolf, *Eur. Jour. Biochem.*, 26, 360 (1972). The rate of pyruvate oxidation is depressed by 50–75% compared with that by diaphragm tissue from rats fed on a normal diet. When L(+)-2-(4-hydroxyphenyl)glycine is added to the medium, it is found to stimulate pyruvate oxidation by diaphragm tissue from fat-fed rats in a dose dependent manner. The threshold concentration for such stimulation is about 0.25 millimolar and a maximum stimulation of 170% is achieved at concentrations of 4 millimolar and above. D(−)-2-(4-hydroxyphenyl)glycine has no significant effect on pyruvate oxidation by diaphragm tissue from fat-fed rats at concentrations up to 4 mM, while the DL (racemic)—compound has an effect approximately half that of the L(+)-isomer.

The degree of stimulation by other compounds of formula (I) at a concentration of 0.5 mM is shown in the following Table:

| Compound | % Stimulation |
|---|---|
| L(+)-2-(4-methoxyphenyl)glycine | 79% |
| Methyl L(+)-2-(4-hydroxyphenyl)glycinate | 89% |
| Isopropyl L(+)-2-(4-hydroxyphenyl)-glycinate | 34% |
| 3-Methylbutyl L(+)-2-(4-hydroxyphenyl)-glycinate | 32% |
| L(+)-2-(4-hydroxyphenyl)glycinamide | 51% |

The following compounds will also be found to stimulate pyruvate oxidation in the above test:
ethyl L(+)-2-(4-methoxyphenyl)glycinate
n-butyl L(+)-2-(4-methoxyphenyl)glycinate
L(+)-2-(4-methoxyphenyl)glycinamide The D-antipodes of the above compounds will be found to have no significant effect on pyruvate oxidation.

EXAMPLE 2

The rate of glucose oxidation by isolated hearts from starved rats is measured in a recirculating oxygenated perfusion system, by measuring the rate of incorporation of carbon-14 from carbon-14-labelled glucose into carbon dioxide using a method similar to those described by Morgan et al., *Jour. Biol. Chem.*, 236, 253 (1961) and by Randle et al., *Biochem. Jour.*, 93, 652 (1962). The perfusate contains glucose, palmitate, insulin and bovine serum albumen. The normal rate of glucose oxidation is found to be 1.27±0.32 micromoles/hour (mean of 9 observations). When L(+)-2-(4-hydroxyphenyl)glycine is included in the perfusate at a concentration of 2 millimolar, the rate of oxidation is increased to 4.77±1.53 micromoles/hour (mean of 9 observations). D(−)-2-(4-hydroxyphenyl)glycine has no significant effect on the rate of oxidation when included in the perfusate at the same concentration.

When the following compounds are employed in place of L(+)-2-(4-hydroxyphenyl)glycine in the above test the rate of glucose oxidation will be significantly increased.
L(+)-2-(4-methoxyphenyl)glycine
n-propyl L(+)-2-(4-hydroxyphenyl)glycinate hydrochloride
DL-2-(4-hydroxyphenyl)glycine, sodium salt
L(+)-2-(4-hydroxyphenyl)glycinamide Glucose oxidation will not be significantly different from the normal rate when comparable levels of D-isomers of the above compounds are employed.

EXAMPLE 3

The ability of the compounds of the invention to increase the proportion of the active form of pyruvate dehydrogenase enzyme has been measured in the following test:

Rats fed on a high fat diet as in Example 1 are treated either with placebo or with the compound of formula (I), by subcutaneous or intravenous injection or by oral administration, and at various times after treatment the rat hearts are removed and homogenized, under conditions which minimize changes in the proportion of the pyruvate dehydrogenase enzyme which is present in the active form, as described by Whitehouse and Randle, *Biochem. Jour.*, 134, 651 (1973). The total amount of the enzyme present (PDHt) and the amount which is present in the active form (PDHa) are assessed by a method similar to that described by Taylor et al., *Jour. Biol. Chem.*, 248, 73 (1973). The fat-feeding process is found to depress the ratio PDHa/PDHt from a normal value of about 0.7 to a value in the range from 0.05 to 0.2. Treatment of fat-fed rats with L(+)-2-(4-hydroxyphenyl)glycine, either parenterally or orally, increases this ratio in a dose-dependent manner, the threshold doses for this effect being 0.05 millimole/kg. by intravenous injection and in the range 0.1 to 0.2 millimole/kg. by subcutaneous injection or by oral administration. The ratio is increased to a value in the range 0.8–1.0 (i.e. above that for rats on normal diet) by doses of 0.6 millimole/kg. and above.

D(−)-2-(4-hydroxyphenyl)glycine has very little effect at dose levels up to 1.2 millimole/kg., while the DL (racemic) compound, although having some activity, has only half, or less than half, the effect of the L(+)-isomer at the same dose levels.

The increase in the PDHa/PDHt ratio effected by other compounds of formula (I) at a dose level of 0.6 millimoles/kg. is shown in the following Table:

| Compound | Dosage Route[1] | PDHa/PDht Ratio Placebo | PDHa/PDht Ratio Compound |
|---|---|---|---|
| Methyl L(+)-2-(4-Hydroxyphenyl) | s.c. | 0.13 | 0.69 |
| | p.o. | 0.13 | 0.42 |

| Compound | Dosage Route[1] | PDHa/PDht Ratio Placebo | PDHa/PDht Ratio Compound |
|---|---|---|---|
| glycinate 3-Methylbutyl L(+)-2-(4-hydroxyphenyl)-glycinate | s.c. | 0.05 | 0.51 |
| L(+)-2-(4-hydroxyphenyl)glycinamide | s.c. | 0.16 | 0.93 |
| | p.o. | 0.16 | 0.91 |

[1] s.c. = subcutaneous; p.o. = oral

In the above test the ratio PDHa/PDHt will also be significantly increased by the following compounds:
L(+)-2-(4-methoxyphenyl)glycinamide
methyl L(+)-2-(4-methoxyphenyl)glycinate gluconate
3-methylbutyl L(+)-2-(4-methoxyphenyl)glycinate hydrobromide
L(+)-2-(4-methoxyphenyl)glycine, potassium salt

EXAMPLE 4

The ability of compounds of formula (I) to reduce oxygen demand and affect the relative utilization of carbohydrate and lipid metabolites in the heart has been assessed by measuring the effect of the compounds on myocardial blood flow and metabolism in fasted, closed-chest, anesthetized beagle dogs, with cardiac catherization to enable simultaneous sampling of coronary sinus and arterial blood to be carried out. Coronary sinus blood flow is measured by the hydrogen gas clearance technique described by Aukland et al., *Circulation Res.*, 14, 164 (1964). The heart is paced electrically at 155 beats/min. and recordings of hemodynamic parameters (blood pressure, left ventricular pressure and the first derivative of the latter) are made continuously. Control measurements of coronary blood flow are made and samples of blood taken at 40 minute intervals, both in an untreated animal and in the same animal dosed with an infusion of isoprenaline (60 mg./kg./min.), which then stimulates cardiac contraction and increases plasma free fatty acid levels. The compound of formula (I) is then administered intravenously and measurements are made and samples taken again, 40 minutes and 90 minutes later. The blood samples from the artery and coronary sinus are analyzed for oxyhemoglobin, pyruvate and free fatty acid (FFA) content, differences between those of the arterial and coronary sinus blood, when multiplied by coronary blood flow, being a measure of oxygen consumption, pyruvate uptake and FFA uptake by the myocardium respectively.

It is found that L(+)-2-(4-hydroxyphenyl)glycine at doses of 0.02 to 0.1 millimole/kg. increases myocardial pyruvate uptake by at least 2-fold, both in the presence and absence of isoprenaline, for a period of at least 90 minutes after dosing, in keeping with its proven action as a PDH stimulator. Myocardial flood flow is simultaneously increased by up to 150%, and myocardial oxygen consumption is decreased by about 20% in the presence of isoprenaline. Myocardial FFA uptake is affected to a variable extent, but is generally decreased. There is no effect on any of the hemodynamic parameters measured.

The following compounds will also be found to have effects similar to L(+)-2-(4-hydroxyphenyl)glycine on myocardial pyruvate uptake, blood flow, oxygen consumption and FFA uptake in this test:
L(+)-2-(4-hydroxyphenyl)glycinamide
L(+)-2-(4-methoxyphenyl)glycine, calcium salt
methyl L(+)-2-(4-hydroxyphenyl)glycinate hydrochloride
3-methylbutyl L(+)-2-(4-hydroxyphenyl)glycinate.

The D-isomers of the above compounds will be found to have no appreciable effect on the above parameters.

EXAMPLE 5

The ability of compounds of formula (I) to decrease blood glucose levels has been assessed by measuring their effect on blood glucose levels in rats in which diabetes has been induced by treatment with streptozotocin (85 mg/kg.). Four days after such treatment, a number of rats are given 1 millimole/kg of the compound by intraperitoneal injection and a similar number are given placebo. The doses are repeated after a further 24 hours and 48 hours. Blood samples are taken from a tail vein immediately before each dosage (which is 2 hours after removal of the animals from food) and 1, 2 and 3 hours after the third dose. After 2 days of treatment with L(+)-2-(4-hydroxyphenyl)glycine (i.e. immediately before the third dose with 1 millimole/kg), blood glucose levels have been found to have declined from 378±8 mg/100 ml. to 356±4 mg/100 ml., compared with a slight increase from 373±8 mg/100 ml. to 383±10 mg/100 ml. for animals treated with placebo; while 2 hours after the third dose the blood levels had declined still further, to a minimum value of 313±7 mg/100 ml., compared with a value of 385±7 mg./100 ml. for animals treated with placebo (all figures are averages for 8 animals).

L(+)-2-(4-methoxyphenyl)glycine as well as the corresponding amide, methyl, 3-methylbutyl and isopropyl esters will give similar reductions in blood glucose levels. The corresponding racemic compounds of formula (I) will give a significant but smaller reduction in blood glucose.

When the D-isomers of 2-(4-hydroxyphenyl)glycine, 2-(4-methoxyphenyl)glycine, and the corresponding amides, methyl, 3-methylbutyl and isopropyl esters are employed, the values obtained will be comparable to those for the rats tested with placebo.

The preparation of unit dosage forms of the compounds of the invention is illustrated by the following Examples.

EXAMPLE 6

Glacial acetic acid (12.0 gm.) and sodium acetate anhydrous (16.4 gm.) were each dissolved in 1000 ml. of freshly distilled water to produce 0.2 molar solutions. 148.0 ml. of the acetic acid solution was then mixed with 352.0 ml. of the sodium acetate solution and the mixture made up to 1000 ml. with freshly distilled water. L(+)-2-(4-hydroxyphenyl)glycine (10.0 gm., 0.056 mole) was then added and the resulting 1% w/v solution of L(+)-2-(4-hydroxyphenyl)glycine had a pH of 5. This was then sterilized by filtration through a suitable bacteria-proof filter under aseptic conditions into sterile 50 ml. glass vials, which when filled with 30 ml. of the final solution, contain 300 mg. of the active ingredient.

EXAMPLE 7

Succinic acid (23.62 gm.) and sodium hydroxide (8 g.) were each dissolved in 1000 ml. of freshly distilled water to produce 0.2 molar solutions. 250 ml. of the succinic acid solution was then mixed with 267.0 ml. of the sodium hydroxide and the mixture made up to 1000 ml. with freshly distilled water. L(+)-2-(4-hydroxyphenyl)glycine (10.0 gm., 0.056 mole) was then added and the resulting 1% w/v solution of L(+)-2-(4-hydroxyphenyl)glycine had a pH of 5. This was then sterilized as in Example 6. Sterile 50 ml. glass vials, when filled with 40 ml. of the final solution, contain 400 mg. of the active ingredient.

EXAMPLE 8

Citric acid monohydrate (21.0 gm.) was dissolved in 200.0 ml. of an 0.1 molar solution of sodium hydroxide in freshly distilled water and the resulting solution was made up to 1000 ml. with freshly distilled and cooled water 963.0 ml. of this solution was then made up to 1000 ml. with an 0.1 molar solution of hydrochloric acid in water. L(+)-2-(4-hydroxyphenyl)glycine (10.0 gm., 0.056 mole) was then added to give a 1% w/v solution having a final pH of 5 at 23° C., which was then sterilized as in Example 6. Sterile 50 ml. glass vials, when filled with 50 ml. of the final solution, contain 500 mg. of the active ingredient.

EXAMPLE 9

750 ml. of freshly distilled water were sparged with nitrogen and then 6.0 g. sodium chloride, 300 mg. of sodium metabisulphite and 15 g. of L(+)-2-(4-hydroxyphenyl)glycine were added successively and stirred to dissolve. The pH was then adjusted to about 4.0 with 0.1 N hydrochloric acid, the solution made up to 1 liter with freshly distilled water and the solution readjusted to pH 4.0±0.35 with 0.1 N HCl, to give a stable, 1.5% w/v isotonic saline solution of the active compound. This was sterilized as in Example 6 and filled into sterile 50 ml. glass vials, which when filled with 50 ml. of solution each contained 750 mg. of the active ingredient. A nitrogen blanket was maintained over the solution throughout and the vials were purged with nitrogen before and after filling.

EXAMPLE 10

Each of the above Examples 6 to 9 is repeated using twice the amount of DL (racemic)-2-(4-hydroxyphenyl)glycine as that of the L(+)-isomer to give solutions containing twice the concentration of active ingredient.

EXAMPLE 11

The following are typical tablet or capsule formulations containing L-(+)-2-(4-hydroxyphenyl)glycine as active ingredient:

|  | mg./tablet or capsule | | | | |
|---|---|---|---|---|---|
|  | A | B | C | D | E |
| Active ingredient | 500 | 100 | 100 | 25 | 25 |
| Lactose | 30 | 170 | — | 220 | — |
| Corn starch | 60 | 80 | — | 105 | — |
| Microcrystalline cellulose ("Avicel") | — | — | 170 | — | 220 |
| Glycine | — | — | 80 | — | 105 |
| Fine silica ("Aerosil") | — | 0.35 | 0.35 | 0.35 | 0.35 |
| Magnesium stearate* | 5 | 3 | 3 | 3 | 3 |
|  | 595 | ... | 353.35 | ... |  |

*9:1 blend with sodium lauryl sulphate
"Avicel" and "Aerosil" are Trademarks.

For formulations A, B and D, the ingredients are thoroughly blended together, and then either filled directly into hard gelatine capsules of appropriate size, or granulated and compressed into tablets of the desired size. For formulations C and E, the ingredients are thoroughly blended together and slugged. The slugs are broken down into granules, and then either filled into capsules of the appropriate size, or directly compressed into tablets of the desired size.

In formulations A, B and D, the lactose may be replaced by equal amounts of calcium carbonate or dicalcium phosphate.

EXAMPLE 12

Example 11 is repeated using the same amount of DL (racemic)-2-(4-hydroxyphenyl)glycine as that of the L(+)-isomer. Of course, twice as many capsules or tablets of this example may be required to be taken for a single therapeutic administration as are required of the tablets or capsules of Example 11.

EXAMPLE 13

Examples 6 to 9 and 11 are repeated using equimolar amounts of the following compounds in place of L(+)-2-(4-hydroxyphenyl)glycine:
L(+)-2-(4-methoxyphenyl)glycine
L(+)-2-(4-methoxyphenyl)glycinamide
Methyl L(+)-2-(4-hydroxyphenyl)glycinate
Isopropyl L(+)-2-(4-hydroxyphenyl)glycinate
2-Methylbutyl L(+)-2-(4-hydroxyphenyl)glycinate
L(+)-2-(4-hydroxyphenyl)glycinamide

EXAMPLE 14

Example 10 is repeated using equimolar amounts of the potassium and hydrochloride salts of L(+)-2-(4-hydroxyphenyl)glycine in place of the free base.

EXAMPLE 15

Examples 10 and 12 are repeated but using equimolar amounts of the following DL (racemic) compounds in place of DL-2-(4-hydroxyphenyl)glycine:
2-(4-methoxyphenyl)glycine
2-(4-methoxyphenyl)glycinamide
methyl 2-(4-hydroxyphenyl)glycinate
isopropyl 2-(4-methoxyphenyl)glycinate
2-methylbutyl 2-(4-methoxyphenyl)glycinate
2-(4-hydroxyphenyl)glycinamide It may advantageous to coat tablets according to the invention with an enteric coating, i.e. a coating of a material such as cellulose acetate-phthalate or hydroxypropylmethyl cellulose phthalate which does not dissolve in the stomach but dissolves in the intestine, and to include in the tablet composition an effervescent material, e.g. sodium bicarbonate and an edible acid such as tartaric acid, in order to avoid de-activation of the active ingredient in the stomach and/or intestine and to enhance the concentration of the active ingredient in the blood.

It may also be desirable to coat tablets with a sugar coating to improve palatability.

EXAMPLE 16

Formation of Cationic Salts

L(+)-2-(4-Hydroxyphenyl)glycine, L(+)-2-(4-methoxyphenyl)glycine or the corresponding DL-compounds are converted to the sodium, potassium, calcium, ammonium, magnesium, arginine, N-methylglucamine, choline, ethanolamine, triethanolamine, triethylamine, piperidine, pyrrolidine, and diethylaminoethylamine salts by reaction with an equivalent amount of the appropriate metal hydroxide, ammonium hydroxide or amine in water, ethanol or mixtures of these solvents. The desired salt is isolated by filtration if it is insoluble or by evaporation of solvent if the salt is soluble therein.

EXAMPLE 17

Formation of Acid Addition Salts

To a solution of L(+)-2-(4-hydroxyphenyl)glycinamide in ethanol is added an equivalent amount of ethanolic hydrogen chloride. The resulting mixture is evaporated to dryness and purified by recrystallization from ethanol/ethyl ether.

By the above procedure any of the amino acids, amino esters or amino amide of formula (I) are converted to the corresponding hydrochloride salt or using the appropriate acid in place of hydrochloric acid the corresponding hydrobromide, sulfate, bisulfate, phosphate, acid phosphate, acetate, maleate, fumarate, lactate, tartrate, citrate, gluconate, succinate, p-toluenesulfonate and carbonate salts are formed.

What is claimed is:

1. A method of treating a mammalian subject suffering from a disease or condition attributable to reduced blood flow or oxygen availability, which comprises orally or parenterally administering to said subject a blood or flow, oxygen availability increasing amount of the L- or DL-form of a compound of the formula:

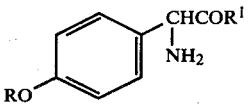

or a pharmaceutically acceptable salt thereof, wherein R is hydrogen or methyl and $R^1$ is $OR^2$, wherein $R^2$ is alkyl having from one to five carbon atoms.

2. A method according to claim 1 wherein said compound is methyl L(+)-2-(4-hydroxyphenyl)glycinate, isopropyl L(+)-2-(4-hydroxyphenyl)glycinate or 3-methylbutyl L(+)-2-(4-hydroxyphenyl)glycinate.

3. A method according to claim 1 wherein said subject is a human and from about 0.5 to 10 mg/kg of the L- form of said compound is administered up to five times a day.

4. A method according to claim 3 wherein said compound is administered orally in the form of tablets or capsules each containing from about 25 to 700 mg. of said compound.

5. A method according to claim 3 wherein said compound is administered parenterally in the form of a solution containing from about 5 to 35 mg. of said compound per ml. of solution.

* * * * *